April 21, 1964 D. STURROCK Plant Pat. 2,391

MANGO

Filed Aug. 20, 1962

DAVID STURROCK

INVENTOR.

BY Hal H McCagh

United States Patent Office

Plant Pat. 2,391
Patented Apr. 21, 1964

2,391
MANGO

David Sturrock, 1020 Camellia Road,
West Palm Beach, Fla.

Filed Aug. 20, 1962, Ser. No. 218,190
1 Claim. (Cl. Pit.—33)

Figure 1:
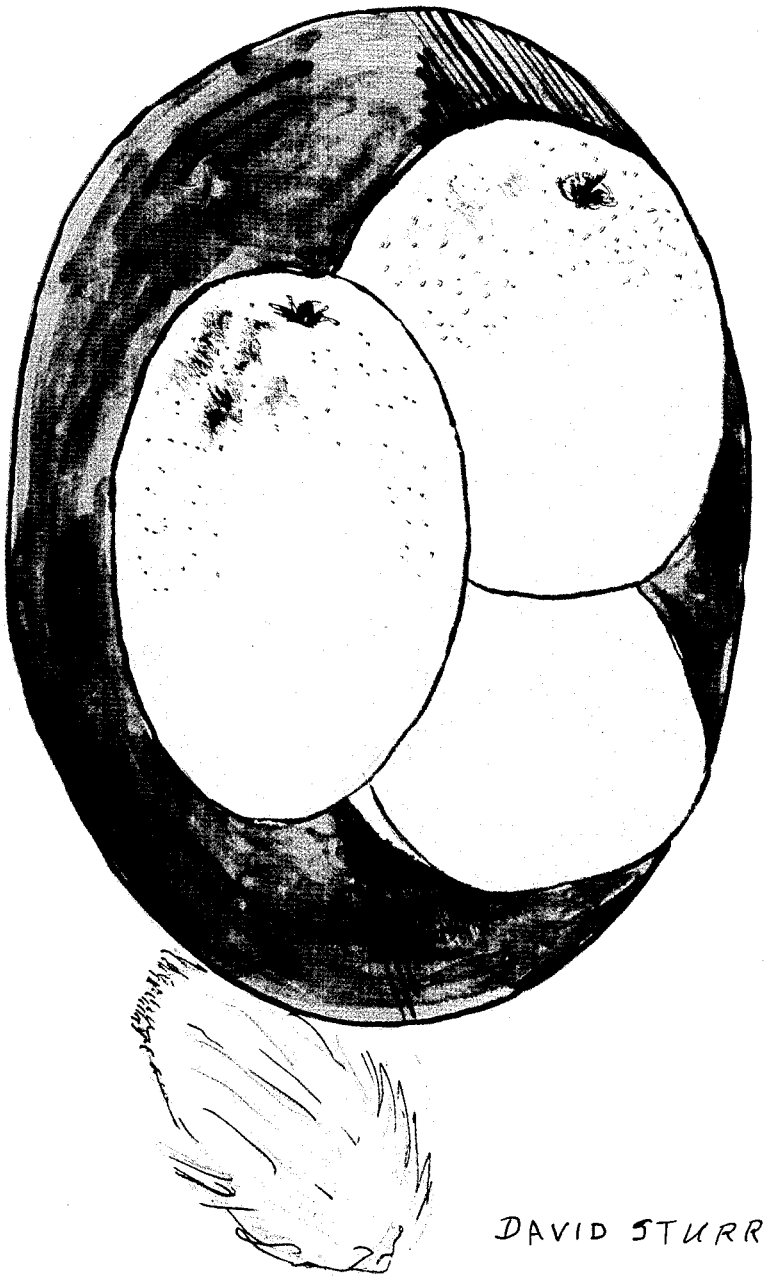

My new variety of mango, *Mangifera indica,* is a result of my planned breeding efforts carried on personally in 1956 and selectively eliminating undesirable progeny and vegetatively propagating the desirable progeny. This variety is a result of crossing the monoembryonic hybrid Edward with the polyembryonic Pico.

The genealogy of this new variety of mango, is:

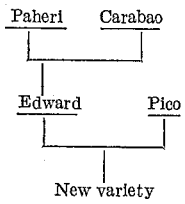

In the flowering season of 1956, branchlets with flower panicles of the Edward variety were marked and mingled with branchlets of the Pico variety having flower panicles. Upon maturity of the marked fruits, the seeds were extracted, hulled and planted. The seedlings, thus obtained, were inspected regularly and those showing susceptibility to scab or anthracnose were discarded. By 1958 there remained fifty seedlings of the original progeny. To hasten maturity for fruiting, these seedlings were fastened and inarched to branches of older mango trees, and the joinder strengthened with rubber bands overlayed with horticultural tape. In 1960, two of these vegetatively propagated varieties fruited; one was discarded as undesirable, and the other vegetatively extended.

The principal distinguishing feature of the variety is the fruit, as illustrated in FIG. 1, showing the color of fruit, the flesh, lack of fibre, and size as compared to a dinner plate on which displayed, and the easily removed seed beside the dinner plate.

The following is a detailed description of the new variety:

*Fruit*

The variety bears fruit in clusters of two to four fruits on short, stout stems, and is uniform in size, shape and color.

It is roundly oval without a pronounced shoulder, has a length of 4½–5 inches and a width of 3¼–3½ inches with a thickness of 3–3¼ inches. Its size is medium, weighing 16–20 ounces.

The base is rounded and the short, stout stem is inserted somewhat obliquely in a slight depression.

The ventral shoulder is more nearly round, and slightly more elevated than other varieties.

The dorsal shoulder slopes steeply.

The apex is rounded.

The nak is inconspicuous, about 1 inch from the apex on the dorsal side.

The skin is a yellow-green color without blush or distinctive markings; medium thick and tough, but readily separated from the flesh.

The flesh is pale amber in color, firm but tender and juicy with a fine smooth texture without fiber in the flesh.

The seed is monoembryonic, filling only the central part of the husk.

The husk is thin, flat at both ends and has short fibers on the dorsal edge.

The season of fruit maturity is July annually.

*Leaf*

The leaf is simple, lanceolate, cariaceous. The blade, without petiole, is 8–10 inches long and 2½–3 inches wide. It is dark green and glossy on the upper surface, and has prominent veins. The blade is slightly twisted and recurved, tapering to a long sharp tip. The base of the blade is rounded and has a stout petiole only 1¼–1½ inches long.

*Shoots*

The tender new leaves and shoots are mauve in color, changing successively to light brown, pale green and then dark green as they mature.

*Flower*

The flower panicles are 12–15 inches in length with short laterals. The mid-stem, laterals and flowers are pale cream in color and do not change color to pink or red on ageing or with direct sunlight. The fruit setting is good with very little shedding at any stage of development.

*Propagation*

This variety is easily propagated vegetatively. The original seedling was inarched high up on a branch of an older tree. After fruiting, side or veneer grafting of young shoots were employed; and thereafter small seedlings were budded to extend the variety. All procedures were successful.

*Disease Resistance*

During the past three years, in the fruiting season, March through July, the variety along with the remaining other hybrids of the same progeny and also others were not sprayed. This variety showed no signs of anthracnose fungus, whereas other varieties were heavily infested, and on many of the other varieties skin lesions developed long before maturity.

By planned breeding, the objective sought was a superior quality mango, prolific in bearing, resistant to climatic conditions and disease, adequate in size and color for commercial purposes; by crossing the monoembryonic East India varieties and hybrids thereof with the smaller, more prolific polyembryonic Philippine varieties. Of the progeny obtained, this variety meets the requirements and characteristics of the objective sought.

All of the above named varieties are unpatented.

Having thus described my invention, what is claimed is:

The variety of mango as described and shown herein.

No references cited.